United States Patent [19]

Brown et al.

[11] Patent Number: 5,201,752
[45] Date of Patent: Apr. 13, 1993

[54] CHOLECYSTECTOMY DISSECTOR INSTRUMENT

[75] Inventors: Michael A. Brown, Bluemont; Joseph McWhinney, Millwood, both of Va.

[73] Assignee: Pod, Inc., Boyce, Va.

[21] Appl. No.: 588,713

[22] Filed: Sep. 27, 1990

[51] Int. Cl.$^5$ ............................................. A61B 17/28
[52] U.S. Cl. .................................. 606/190; 606/207; 606/170; 128/751
[58] Field of Search ............... 606/207, 208, 205, 206, 606/170, 171, 142, 190; 128/751

[56] References Cited

U.S. PATENT DOCUMENTS

| | | |
|---|---|---|
| 2,113,246 | 4/1938 | Wappler . |
| 3,446,211 | 5/1969 | Markham ............................ 606/207 |
| 3,585,985 | 6/1971 | Gould ................................... 606/208 |
| 4,644,951 | 2/1987 | Bays ..................................... 606/170 |
| 4,669,471 | 6/1987 | Hayashi . |

FOREIGN PATENT DOCUMENTS 464306  3/1975  U.S.S.R. ............................ 606/190

OTHER PUBLICATIONS

Mueller "The Surgical Armamentarium" (1980) pp. 90, 91, 237, 289, 1084.
Solos Endoscopy, Laparoscopic Cholecystectomy.

*Primary Examiner*—Michael H. Thaler
*Attorney, Agent, or Firm*—Laurence R. Brown

[57] ABSTRACT

A specialty surgical instrument for engaging, spreading and removing tissue surrounding an exposed cystic duct and artery in an endo cholecystectomy dissection procedure is provided by this invention. An ergonomically superior scissors action handle extends perpendicular to a cylindrical body for receiving the thumb and two fingers of a surgeon for better control in manipulating a coaxial rod inside the body to operate double action forceps jaws of special design for the dissection of the cystic duct and artery from liver bed tissue, with the feel of the surgeon as if the balance of the instrument and its jaws are an extension of the surgeon's fingers. The jaws have a shape and roughened exterior finish for frictionally engaging tissue in the vicinity of the cystic duct and adjacent artery and spreading it during the dissection procedure. The interior of the jaws are serrated and mated in mutual contact surfaces in closed position to frictionally grasp tissue and bladder for removal. The jaws are specially curved for fitting the anatomical shape of the gall bladder tissue terrain for producing a planar surface in the gall bladder tissue from which the cystic duct and artery are dissected and for cradling the cystic duct during dissection. The length of the jaws permits tissue to be spread significant distances apart for prying tissue surfaces apart. The general exterior jaw shape prevents traumatic damage to the tissue during the dissection procedure and thus bleeding during the procedure.

13 Claims, 2 Drawing Sheets

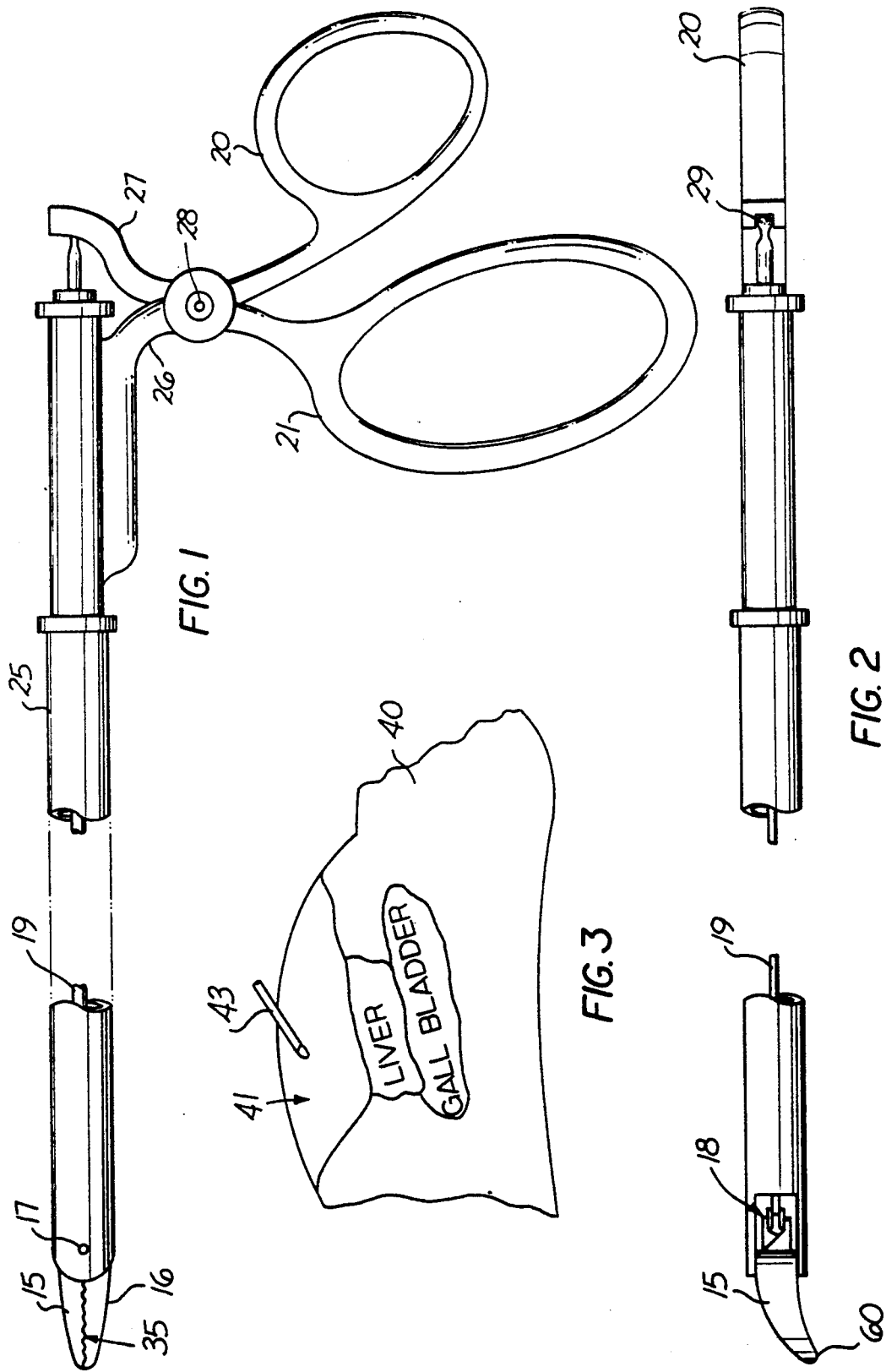

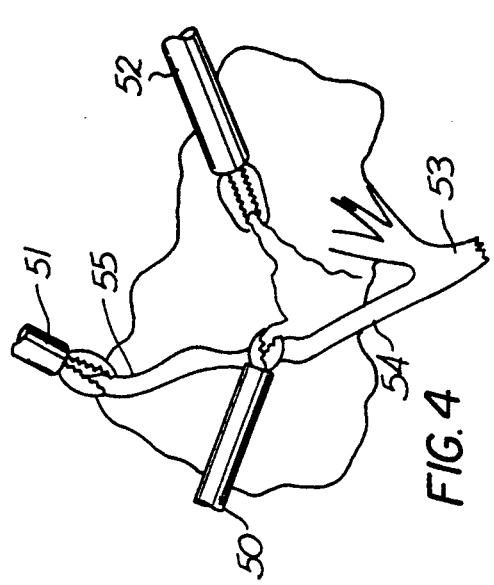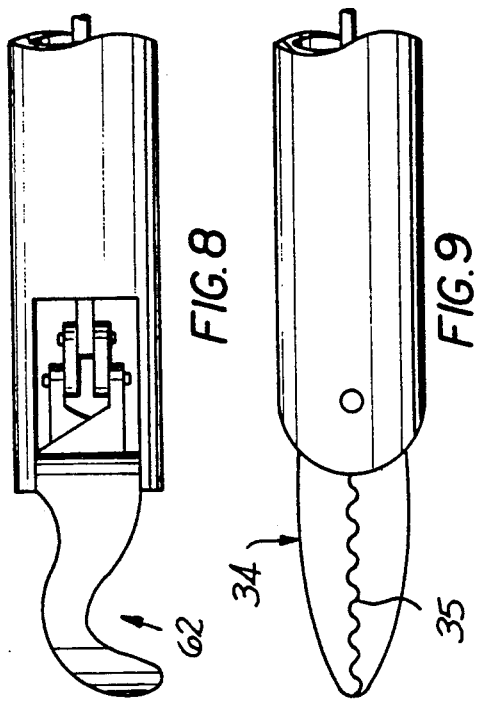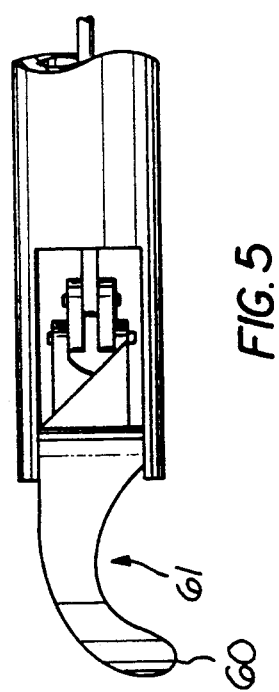

CHOLECYSTECTOMY DISSECTOR INSTRUMENT

TECHNICAL FIELD

This invention relates to surgical instruments and more particularly it relates to a specialty cholecystectomy dissector instrument for grasping, spreading and removing tissue surrounding a cystic duct and adjacent artery of the gall bladder.

BACKGROUND ART

"Buttonhole" surgery for gallbladder disease has been developed with laparoscopic cholecystectomy techniques for which commercial equipment is now available including several types of specialty surgical instruments. A line of instruments and equipment is available for endo cholecystectomy from SOLOS Endoscopy, Inc. of Norcross, Ga., for example. One such instrument, introduced by Karl A. Zucker, MD, of Maryland University for dissecting the cystic duct and ajacent artery from tissue in the vicinity of the gall bladder has become known as the "Maryland" dissector. This instrument essentially comprises alligator jawed forcep with a slightly curved end point.

This forcep is used by introduction into the abdominal cavity through a trocar sleeve for the explicit purpose of dissecting an exposed cystic duct and artery in the process of an endo cholecystectomy. The present invention provides a specialty instrument of this type with improved features facilitating surgical treatment of gallbladder disorders.

General types of surgical forceps are known in the art such as disclosed in U.S. Pat. No. 2,113,246, F. C. Wappler, Apr. 5, 1938, wherein forcep jaws are manipulated by means of scissor type handles extending laterally from a tubular housing with an enclosed reciprocating actuating rod connected respectively with the scissor lever arms. Various linkages for operating the forcep jaws are described for example in U.S. Pat. No. 4,669,471, S. Hayashi, Jun. 2, 1987. These jaws may be either spring biased or double acting to move freely in both opening and closing directions by means of surgeon's fingers in the scissor handles.

Since it is early in the development of endo cholecystectomy techniques the specialty instruments have been introduced in primitive form, and thus have deficiencies in actual practice under varying conditions encountered because of differences in patient anatomy, surgeon's skills, etc. Accordingly it is an objective of this invention to provide an improved surgical instrument of the foregoing "Maryland" dissector type that better suits the needs of the patient and surgeon. The improvements afforded by this instrument will be set forth throughout the following description, claims and accompanying drawings.

DISCLOSURE OF THE INVENTION

The specialty cholecystectomy forcep instrument for grasping, spreading, dissecting and removing tissue surrounding an exposed cystic duct and adjacent artery is adapted to pass into the abdominal cavity through a trocar sleeve of about 11 mm diameter, and is thus housed in a cylindrical tubing body of about ten mm diameter. This instrument is manipulated by one of two attending surgeons for finding, grasping, positioning and dissecting the cystic duct and associated artery from adjoining liver bed tissue, while an associate surgeon holds the gall bladder in place with other instrumentation, to be exposed to view by an endoscope display panel while the operation is taking place.

This instrument has double action forcep jaws operable from a scissors grip handle extending perpendicular to the cylindrical instrument body and providing a thumb ring and two-finger finger ring for increased surgeon strength and feel. The associated jaws are extended in length and shaped for wider spreading of adjacent tissue when the jaws are opened wider, are shaped to fit the natural terrain of the liver bed area from which the gall bladder and associated organs are being dissected for a range of different patient anatomies, and are driven by a mechanism that permits the surgeon to use the instrument as naturally as if it were an extension of the fingers.

The exterior surface of the jaws is roughened for frictionally gripping the gall bladder and tissue thereabout to spread it and is rounded and shaped explicitly with surrounding terrain to avoid trauma and to reduce bleeding about the duct and artery. The inner surface of the jaws is serrated and mated for close fitting surface contact so that small bits of tissue can be grasped and moved or removed and so that the gall bladder can be positively grasped in the process of removal through the trocar sleeve portal after dissection from the liver bed.

Other features, advantages and objectives of the invention will be found in the following description.

BRIEF DESCRIPTION OF THE DRAWINGS

In the accompanying drawing:

FIG. 1 is a partly broken away side view of a surgical instrument afforded by this invention looking into the plane of the scissors grip handle, FIG. 2 is a similar side view with the handle rotated 90 degrees, FIG. 3 is a diagrammatic sketch, partly broken away of a patient undergoing endo cholecystectomy, FIG. 4 is a sketch illustrating the dissection procedure with the gall bladder cystic duct and artery exposed, with the dissecting forcep instrument in use, and FIG. 5 through 9 are fragmental views illustrating forcep jaw shapes provided in accordance with this invention for following the natural terrain of the gall bladder undergoing surgery and particularly adapted for dissection of the cystic duct and adjacent artery from the adjacent liver bed.

THE PREFERRED EMBODIMENTS OF THE INVENTION

As may be seen from FIGS. 1 and 2, curved forcep jaws 15, 16 are pivoted back and forth in double action movement about an axis defined by pivot pin 17 by a mechanism 18, when actuating rod 19 is reciprocated by a surgeon manipulating the scissor grip handle thumb ring 20 and finger ring 21. A cylindrical housing 25 of about ten mm diameter to extend through an eleven mm trocar sleeve concentrically shares an axis with the actuating rod 19. The handle lever arms 26, 27 are pivoted at axis pin 28 with a ball-socket mechanism 29 coupling arm 27 to the reciprocating rod 19.

With the two finger grip ring 21, the surgeon can apply more force and more natural finger feel than with a one finger ring, and is thus advantageous for spreading apart tissue or for gripping tightly small pieces of tissue or the gall bladder when being dislodged for removal through a small incision in a natural manner that stimulates the extension of the surgeon's fingers to move the jaws open and closed. The lever arm 26 is affixed to housing 25 to permit the thumb ring 20 to extend beyond the end of the housing, whereas the finger ring 21 is positioned near the end, but overlapping with the body 25 to form a balancing grip adapted to facilitate the special surgical procedure of spreading and dissecting the cystic duct and artery tissue of the gall bladder from the patient. The resulting instrument balance is extremely critical to reduce fatigue of the surgeon and to permit precise positioning within the abdominal cavity through the portal in a natural and comfortable manner. The overall length is not critical, but is typically in the range of 30 to 40 cm. The length of the jaws is preferably about 15 to 30 mm from the pivot axis. All materials are preferably surgical stainless steel, but can be other materials of sufficient strength that will not degrade when disinfected in steam autoclaves or soaking fluids, and which are adapted to safe surgical practice.

The bearings for rod 19, mechanism 18, etc. are adjusted for free reciprocating movement of the jaws 15, 16 with kinestetic feedback to the surgeon when in use to permit a natural feel for the different surgical functions of the instrument, so that surgical expertise will naturally follow without significant practice.

The jaws 15, 16 have a roughened, frictional exterior surface 34 for firm contact with the tissue about the cystic duct in the spreading function. The edges and end portions of the jaws are rounded and curved with a shape that avoids trauma and scraping damage to the tissue about the cystic duct and artery, and thus reduces accompanying bleeding that could occlude the view. The jaws 15, 16 are long enough and have accompanying shape at tip 60 to extend between or around the duct and artery after penetration for visibly viewing in the laparoscope screen.

The interior jaw surface 35 is serrated and mated to close in substantially full surface contact. This facilitates the grasping of small pieces of tissue that hinder the view, for example, to remove or reposition, and provides a firm grip on the gall bladder neck after transection and for assisting removal of the gall bladder from the abdominal cavity through a small incision. The double action of the jaws permits more effective use of surgical and anasthesia time by spreading more tissue without continuous respositioning procedure.

These features and their advantages in use will be more particularly appreciated when reviewing the surgical procedure in the endo cholecystectomy dissection procedure for which the instrument of this invention is provided. Thus, in FIG. 3, the patient 40, is shown with an abdominal cavity region 41 expanded by three or four liters of $CO_2$ under 12-14 mm Hg pressure, for example, for entry of the laparoscope 43 through a trocar sleeve, not shown, to view the gall bladder and liver bed during the operation, as the gall bladder is separated from the surrounding liver bed tissue and detached. The patient is suitably turned for best access, and at least two surgical instruments are entered through other incisions for use by two surgeons located on opposite sides of the patient.

Thus, the critical operation region at the gall bladder site, together with the inserted surgical instruments, are viewed on a laporoscope screen in a manner such as seen in FIG. 4. It is necessary to dissect tissues about the cystic duct 54 (near the tip of probe 50) and adjacent artery 55 to expose them for detachment of the gall bladder. Thus, the probes 50 or 51 may be grasping forceps used by the helper surgeon to hold portions of the tissue or gall bladder in place for viewing or surgical procedure during the dissection with the remaining dissecting probe 52, which is the subject of this invention.

Thus, the dissecting probe 52 of this invention functions to grasp tissue between its jaw to position it or tear it away, to spread apart tissue or to pull the artery of cystic duct away from the adjoining liver bed by opening the jaws, to be inserted under the cystic duct 54 (shown at the end of probe 50) and artery 55 (shown at the tip of probe 51) with closed jaws to separate them from the liver bed tissue and to grip dissected organs to place them for viewing or incision or cutting and clipping, and furthermore to create, smooth and shape the liver bed plane from which the gall bladder is dissected and removed by cutting away from the common bile duct 53 and artery 55.

Thus, the dissecting probe, grasps, positions, spreads, removes and prepares the surface of tissue during the endo cholecystectomy procedure. For achieving such functions, the exterior surface texture of the jaws and the grasping serrations on the internal surface are critical, as hereinbefore described.

It is also to be recognized that the natural terrain of the liver bed area about the gall bladder will vary from patient to patient. The size of the artery or cystic duct is different for males and females for example. Also it has been discussed that one function of the instrument afforded by this invention is for insertion under the cystic duct 54, and artery 55 to dissect them from the liver bed. The shape and contour of the jaws is therefore critical. Accordingly the jaw embodiments of FIGS. 5 through 9 permit the dissector forceps of this invention to be more versatile and assist the surgeon in producing a lower risk and more professional treatment and/or removal of the gall bladder. The top side of the jaws as shown in the drawing are shaped for nesting in the plane of the liver bed from which the cystic duct 54 and artery 55 are dissected, and the lower side of the jaws cradle the duct and artery to pull it away from the liver bed tissue, and the like.

The jaws thus are characterized by the substantially C-shaped curvature of FIG. 5, the substantially J-shaped curvature of FIGS. 6 and 7, and the substantially S-shaped curvature of FIG. 8, as shown in the preferred embodiments, when viewed in profile. The top view of FIG. 9 shows the critical exterior surface 34 and the serrated mating jaw surfaces 35. In all the views, the absence of sharp edges and corners is critical to reduce trauma and accompanying bleeding and to decrease tissue damage in the dissection procedure.

Common to the various jaw embodiments is a generally hooked end 60, defined for example at the end of the C-shaped curvature 61 of the jaw in FIG. 5. This serves the purpose of probing underneath the cystic duct and artery to initiate dissection, and to rest them in the cradle on the lower side of the jaw to pry them from the liver bed tissue, and the rounded surfaces permit these organs to be dissected from the liver bed with minimal tissue damage and disorientation.

The shape of the hook 60 varies from FIGS. 5 through 7 so that the particular anatomy or terrain of a patient may be matched for best results. The relatively sharper hook point of the FIG. 7 or 8 jaw may be preferable for insertion under the duct or artery. The C- shaped hollow 61 of FIG. 5 may be preferred for moving longitudinaly along the duct or artery for dissection from the liver bed larger size organs. The S-shape of FIG. 8 provides a smaller cupped hollow 62 for serving this purpose and is particularly useful for smaller diameter ducts.

It is therefore seen that this invention has produced a superior specialty surgical dissection instrument particularly adapted for endo cholecystectomy. Those novel features defining the spirit and nature of this invention are thus set forth with particularity in the following claims.

We claim:

1. A surgical specialty instrument having dimensions for insertion into the abdomen when expanded under pressure through an eleven mm trocar sleeve for comfortable manipulation by a surgeon in spreading and removing tissue surrounding an exposed cystic duct and artery in an endo cholecystectomy dissection procedure, comprising in combination:
    a handle having two lever arms pivotable about a common pivot axis respectively defining at one end of each lever arm a separate ring for actuation by a surgeon to relatively move the two lever arms back and forth over a predetermined working arc,
    a tubular body affixed at an end to a first lever arm of a length, diameter, and construction for insertion through an incision into the abdominal body cavity by means of said trocar sleeve, said tubular body having a length of between 30 and 40 cm in order to reach the gall bladder, when the abdomen is expanded, with handle room for a surgeon to manipulate the tubular body during said procedure,
    a set of jaws pivotably mounted on the tubular body to move about a pivot axis at an end of the body opposite the handle,
    means for pivoting the jaws in a double action movement respectively for spreading apart and gripping tissue responsive to the movement of the lever arms in opposite directions comprising a rod coaxially movable within said body connected to the second one of the lever arms, and
    jaw structure comprising said set of jaws having an exterior finish for frictionally engaging and spreading tissue located in the vicinity of the cystic duct and adjacent artery and (b) serrated jaw teeth for mating the two jaws in substantially full surface contact in closed position and for frictionally grasping and moving tissue as forceps in response to manipulation of the lever arms by a surgeon's fingers in the handle,
    said jaws having an exterior shape substantially curving at a hook end away from the axis of the rod and body of a contour for fitting snugly around the cystic duct and artery of a patient and adapted for spreading and grasping tissue respectively by opening and closing of the double action jaws in a dissection procedure in the cystic duct and artery region, the exterior shape exhibiting a curvature being defined by rounded edges and end surfaces to reduce traumatic damage to tissue-contacted in the dissection procedure.

2. The instrument of claim 1 wherein the exterior jaw shape tapers in thickness from a mount position on the body toward its end, and curves away from the common rod and body axis from a position along the common rod and body axis remote from the pivot axis.

3. The instrument of claim 1 wherein the exterior jaw shape includes a substantially S-shaped curve extending outwardly from the pivot axis of the jaws.

4. The instrument of claim 1 wherein the exterior jaw shape includes a substantially C-shaped curve extending outwardly from the pivot axis of the jaws.

5. The instrument of claim 1 wherein the exterior jaw shape includes a substantially J-shaped curve extending outwardly from the pivot axis of the jaws.

6. The instrument of claim 1 wherein the exterior jaw shape conforms to the cystic duct within the gall bladder.

7. The instrument of claim 1 wherein the two arms of said handle extend substantially perpendicular to the tubular body.

8. The instrument of claim 1 wherein one handle lever arm comprises a finger ring accommodating two fingers of a surgeon.

9. The instrument of claim 8 wherein a thumb ring is on the second lever arm affixed to the outer surface of said body, the finger ring is positioned within the length of the body, and the thumb ring is positioned outside the length of the body.

10. A special purpose endo cholecystectomy dissection forcep instrument for manipulating a cystic duct and for spreading and removing tissue by means of two double acting jaws each of which is shaped with a hooked end profile, said jaws being mounted on a forcep body dimensioned for inserting into an expanded stomach cavity during endo cholecystectomy thereby to located said jaws beneath the cystic duct to snugly grasp and hold the cystic duct by means of a hollow cradle dimensioned by the hooked end for fitting about the cystic duct of the gall bladder, a mechanism for operating said jaws by a surgeon from the outside of the stomach cavity comprising a manually operable handle on the forcep body coupled to the mechanism for operating said jaws.

11. The instrument of claim 10 wherein the jaws are long enough and the hook is shaped so that the jaws penetrate beneath and surround the cystic duct with a tip visible for viewing the position of the hooked jaw tip.

12. The instrument of claim 10 with exterior jaw surfaces roughened for frictionally gripping the gall bladder and surrounding tissue when used as a spreader.

13. The instrument of claim 10 having a cylindrical body between 30 and 40 cm in length of a diameter no greater than 10 mm for manipulation through a trocar of 11 mm diameter.

* * * * *